US011057559B2

(12) United States Patent
Ono

(10) Patent No.: US 11,057,559 B2
(45) Date of Patent: Jul. 6, 2021

(54) ENDOSCOPE AND ENDOSCOPE SYSTEM

(71) Applicant: OLYMPUS CORPORATION, Tokyo (JP)

(72) Inventor: Makoto Ono, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/822,883

(22) Filed: Mar. 18, 2020

(65) Prior Publication Data
US 2020/0221023 A1 Jul. 9, 2020

Related U.S. Application Data

(63) Continuation of application No. PCT/JP2018/018969, filed on May 16, 2018.

(30) Foreign Application Priority Data

Sep. 19, 2017 (JP) .............................. JP2017-179291

(51) Int. Cl.
| | |
|---|---|
| A61B 1/00 | (2006.01) |
| G02B 23/24 | (2006.01) |
| H03L 7/099 | (2006.01) |
| H04N 5/232 | (2006.01) |
| H04N 5/06 | (2006.01) |
| H04N 5/378 | (2011.01) |

(Continued)

(52) U.S. Cl.
CPC ..... *H04N 5/23227* (2018.08); *A61B 1/00006* (2013.01); *A61B 1/00009* (2013.01); *A61B 1/045* (2013.01); *A61B 1/05* (2013.01); *H03L 7/0992* (2013.01); *A61B 1/00032* (2013.01); *A61B 1/00045* (2013.01); *A61B 1/00114* (2013.01); *H04N 2005/2255* (2013.01)

(58) Field of Classification Search
USPC .......................................................... 348/76
See application file for complete search history.

(56) References Cited

U.S. PATENT DOCUMENTS

| | | | |
|---|---|---|---|
| 2012/0320177 A1* | 12/2012 | Nishimura | ........... H04N 5/0675 348/65 |
| 2014/0285645 A1 | 9/2014 | Blanquart et al. | |
| 2016/0295141 A1* | 10/2016 | Sone | ........................ H04N 7/18 |

FOREIGN PATENT DOCUMENTS

| | | |
|---|---|---|
| JP | 2000-165759 A | 6/2000 |
| JP | 2016-520341 A | 7/2016 |
| WO | 2014/145246 A1 | 9/2014 |

OTHER PUBLICATIONS

Jul. 3, 2018 Search Report issued in International Patent Application No. PCT/JP2018/018969.

* cited by examiner

Primary Examiner — Patricia I Young
(74) Attorney, Agent, or Firm — Oliff PLC

(57) ABSTRACT

An endoscope includes an imaging circuit that generates an imaging signal. The endoscope has a transmission path that connects the imaging circuit to a control device to perform image processing on the imaging signal. The endoscope also includes a phase synchronization unit having (i) a digital control oscillator that generates a drive clock signal, and (ii) a phase digital output circuit that generates and outputs a phase digital signal to the transmission path. A first switch of the endoscope connects the transmission path to one of the control device and the phase digital output circuit, and a second switch connects the transmission path to one of the imaging circuit and the digital control oscillator.

7 Claims, 12 Drawing Sheets

(51) Int. Cl.
*A61B 1/045* (2006.01)
*A61B 1/05* (2006.01)
*H04N 5/225* (2006.01)

ENDOSCOPE AND ENDOSCOPE SYSTEM

CROSS-REFERENCE TO RELATED APPLICATION

This application is a continuation of PCT International Application No. PCT/JP2018/018969 filed on May 16, 2018, which designates the United States, incorporated herein by reference, and which claims the benefit of priority from Japanese Patent Application No. 2017-179291, filed on Sep. 19, 2017, incorporated herein by reference.

BACKGROUND

1. Technical Field

The present disclosure relates to an endoscope that captures an object to generate the image data on the object and to an endoscope system.

2. Related Art

In the related art, there is a technique for an endoscope system to transmit signals from a processor to an endoscope via a transmission cable (see Japanese Laid-open Patent Publication No. 2000-165759). According to this technique, reference clock signals generated by the processor are transmitted via a transmission cable to the distal end portion of the endoscope including a charge coupled device (CCD).

SUMMARY

In some embodiments, an endoscope includes an imaging circuit configured to execute photoelectric conversion on received light to generate an imaging signal; a transmission path configured to connect the imaging circuit to a control device configured to perform image processing on the imaging signal generated by the imaging circuit so as to transmit the imaging signal; a phase synchronization unit including: a digital control oscillator that is provided at a side of a distal end of the transmission path, the digital control oscillator being configured to generate a drive clock signal that drives the imaging circuit; and a phase digital output circuit that is provided at a side of a proximal end of the transmission path, the phase digital output circuit being configured to generate a phase digital signal that controls an oscillation frequency of the drive clock signal generated by the digital control oscillator based on a phase difference between a reference clock signal and the imaging signal, and the phase digital output circuit is configured to output the generated phase digital signal to the transmission path; a first switch that is provided at the side of the proximal end of the transmission path, the first switch being configured to connect the transmission path to one of the control device and the phase digital output circuit; a control unit configured to: cause the first switch to connect the transmission path to the control device in an imaging signal transmission time period for transmitting the imaging signal, and cause the first switch to connect the transmission path to the phase digital output circuit in a time period other than the imaging signal transmission time period; a second switch that is provided at the side of the distal end of the transmission path, the second switch being configured to connect the transmission path to one of the imaging circuit and the digital control oscillator; and a timing control signal generating circuit configured to: cause the second switch to connect the transmission path to the imaging circuit in the imaging signal transmission time period, and cause the second switch to connect the transmission path to the digital control oscillator in the time period other than the imaging signal transmission time period.

In some embodiments, an endoscope system includes an endoscope including: an imaging circuit configured to execute photoelectric conversion on received light to generate an imaging signal; and an insertion part configured to be inserted into a subject, the insertion part including the imaging circuit at a distal end portion of the insertion part; a timing control signal generating circuit configured to generate a drive signal to drive the imaging circuit; a control device configured to perform image processing on the imaging signal generated by the imaging circuit; a transmission path configured to connect the imaging circuit to the control device to transmit the generated imaging signal; a phase synchronization unit including: a digital control oscillator that is provided at a side of a distal end of the transmission path, the digital control oscillator being configured to generate a drive clock signal for the timing control signal generating circuit to generate the drive signal; and a phase digital output circuit that is provided at a side of a proximal end of the transmission path, the phase digital output circuit being configured to generate a phase digital signal that controls an oscillation frequency of the drive clock signal generated by the digital control oscillator based on a phase difference between a reference clock signal and the imaging signal, the phase digital output circuit being configured to output the phase digital signal to the transmission path; a first switch that is provided at the side of the proximal end of the transmission path, the first switch being configured to connect the transmission path to one of the control device and the phase digital output circuit; a control unit configured to: cause the first switch to connect the transmission path to the control device in an imaging signal transmission time period for transmitting the imaging signal, and cause the first switch to connect the transmission path to the phase digital output circuit in a time period other than the imaging signal transmission time period; and a second switch that is provided at the side of the distal end of the transmission path, the second switch being configured to connect the transmission path to one of the imaging circuit and the digital control oscillator, the timing control signal generating circuit causing the second switch to connect the transmission path to the imaging circuit in the imaging signal transmission time period, and the timing control signal generating circuit causing the second switch to connect the transmission path to the digital control oscillator in the time period other than the imaging signal transmission time period.

The above and other features, advantages and technical and industrial significance of this disclosure will be better understood by reading the following detailed description of embodiments of the disclosure, when considered in connection with the accompanying drawings.

DETAILED DESCRIPTION

Figure 1:
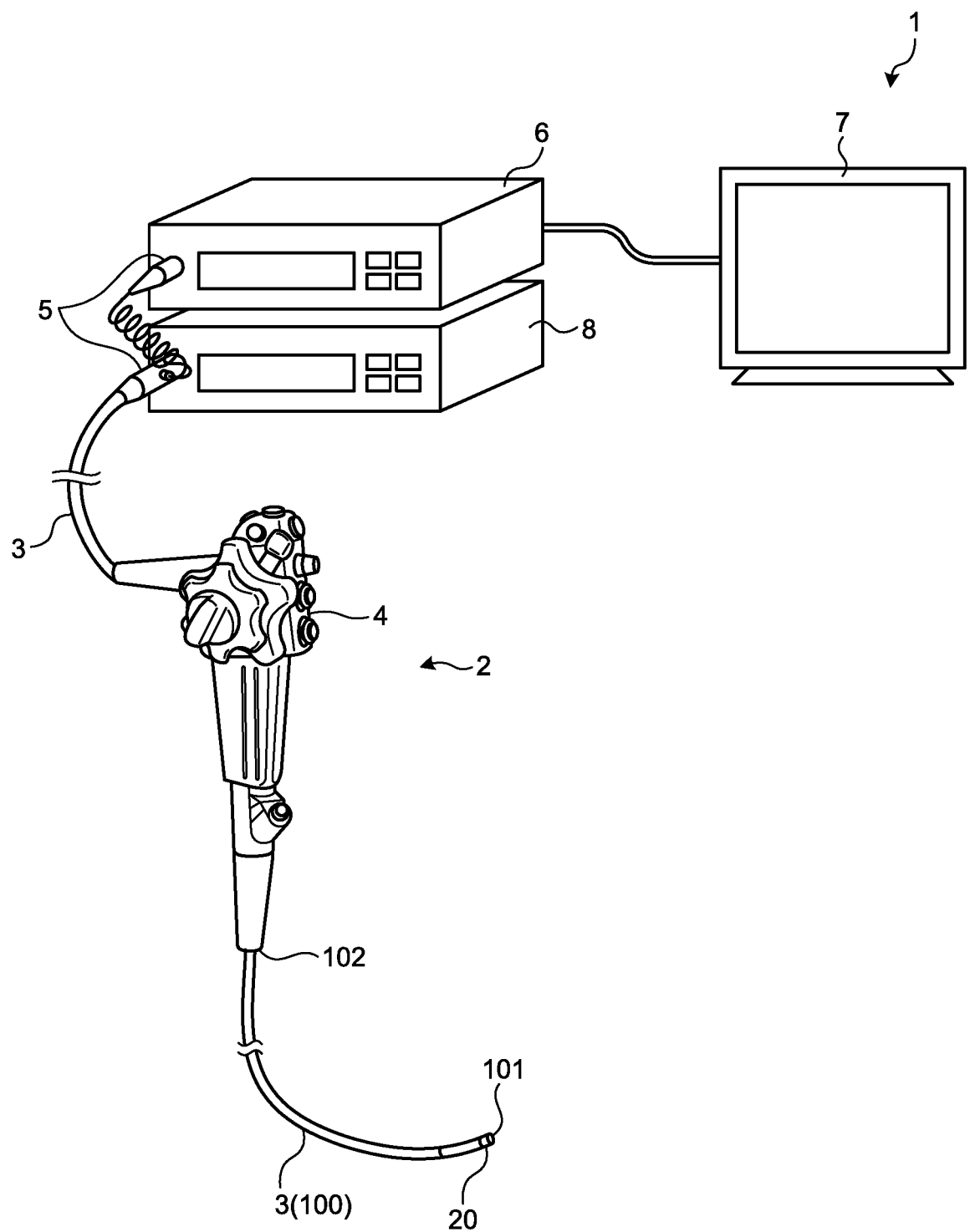
FIG. 1 is a schematic diagram illustrating a general configuration of an endoscope system according to a first embodiment.

With reference to the drawings, configurations (hereinafter referred to as "embodiments") for carrying out the disclosure are described below in detail. The disclosure is not limited to the embodiments described below. Each of the figures referred to in the description below schematically illustrates the shape, the size, and the positional relationship so as to understand the details of the disclosure. That is, the disclosure is not limited to the shapes, the sizes, and the positional relationships illustrated in the drawings. An endoscope system including a flexible endoscope is described below as an example of the endoscope system.

First Embodiment

Configuration of the Endoscope System

FIG. 1 is a schematic diagram illustrating a general configuration of an endoscope system 1 according to a first embodiment. The endoscope system 1 illustrated in FIG. 1 includes an endoscope 2, a transmission cable 3, a connector unit 5, a processor 6 (control device), a display device 7, and a light source device 8.

The endoscope 2 captures the inside of the subject's body to generate an imaging signal (image data) and then outputs the imaging signal to the processor 6 when an insertion part 100, which is part of the transmission cable 3, is inserted into the body cavity of the subject. In the endoscope 2, an imaging unit 20 that captures the body cavity of the subject to generate an imaging signal is provided at one end side of the transmission cable 3 and at the side of a distal end 101 of the insertion part 100 inserted into the body cavity of the subject, and an operating unit 4 that receives various operations on the endoscope 2 is connected to the side of a proximal end 102 of the insertion part 100. An imaging signal generated by the imaging unit 20 is output to the connector unit 5 via the transmission cable 3 having a length of at least 10 cm.

The connector unit 5 is removably connected to the processor 6 and the light source device 8 to perform predetermined signal processing on the image data output from the imaging unit 20 and output it to the processor 6.

The processor 6 performs predetermined image processing on an imaging signal input from the connector unit 5 to output it to the display device 7 and integrally controls the entire endoscope system 1.

The display device 7 displays various information regarding the endoscope system 1 and the image corresponding to the imaging signal captured by the endoscope 2 under the control of the processor 6.

The light source device 8 emits illumination light under the control of the processor 6. The light source device 8 includes, for example, a halogen lamp or a white LED (light emitting diode) to emit illumination light toward the subject from the distal end 101 of the insertion part 100 of the endoscope 2 via the connector unit 5 and the transmission cable 3.

Functional Configuration of the Relevant Part of the Endoscope System

Figure 2:
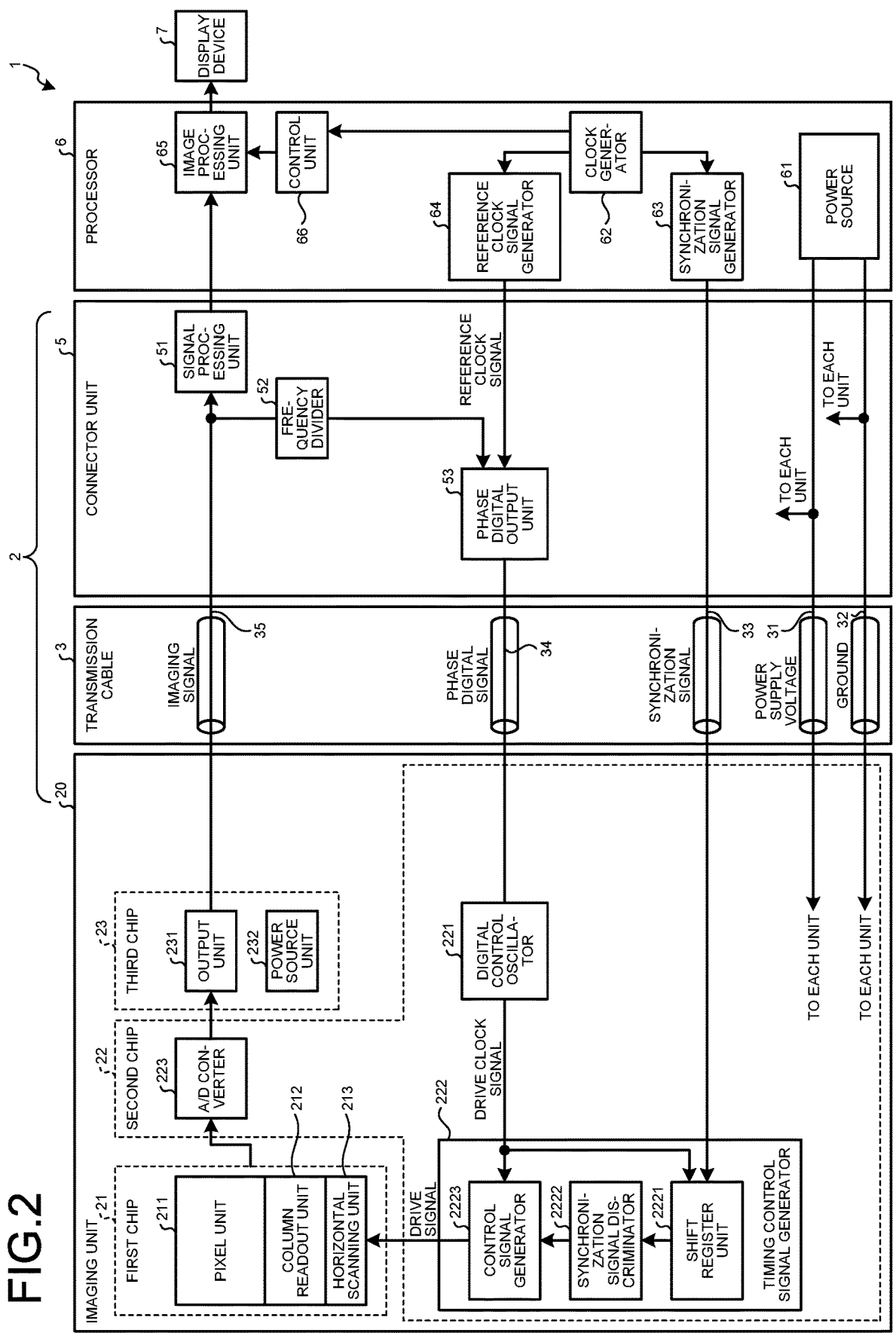
FIG. 2 is a block diagram illustrating a functional configuration of the relevant part of the endoscope system according to the first embodiment.

Next, a functional configuration of the relevant part of the endoscope system 1 described above is described. FIG. 2 is a block diagram illustrating a functional configuration of the relevant part of the endoscope system 1.

Configuration of the Endoscope

First, the endoscope 2 is described.

As illustrated in FIG. 2, the endoscope 2 includes at least the imaging unit 20, the transmission cable 3, and the connector unit 5.

Configuration of the Imaging Unit

First, a configuration of the imaging unit 20 is described.

Figure 3A:
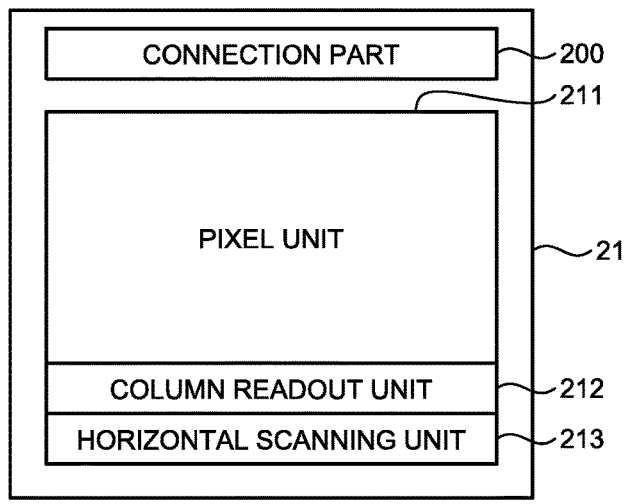
FIG. 3A is a plan view schematically illustrating an example of the arrangement of functional devices of a first chip according to the first embodiment.
Figure 3B:
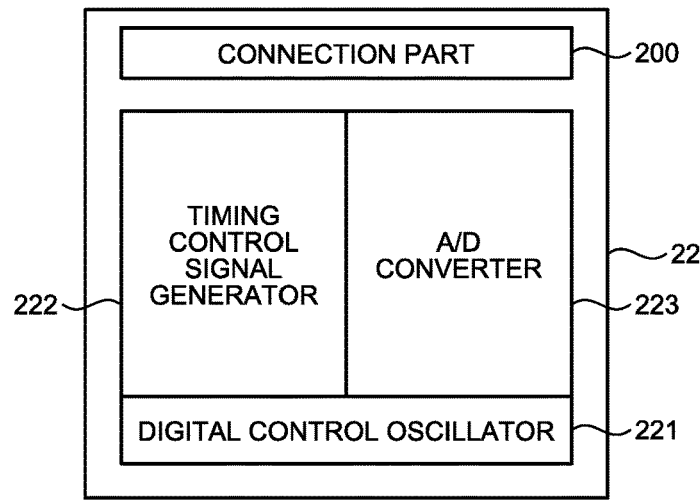
FIG. 3B is a plan view schematically illustrating an example of the arrangement of functional devices of a second chip according to the first embodiment.
Figure 3C:
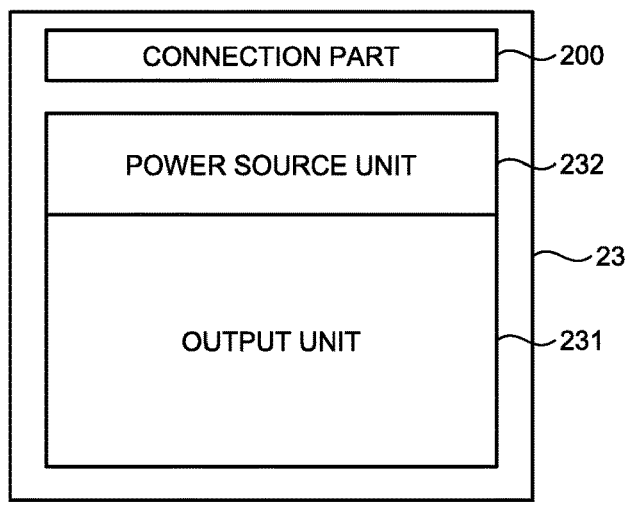
FIG. 3C is a plan view schematically illustrating an example of the arrangement of functional devices of a third chip according to the first embodiment.

As illustrated in FIG. 2, the imaging unit 20 is a semiconductor substrate that includes, for example, a first chip 21 (an imager substrate), a second chip 22 (a readout circuitry substrate), and a third chip 23 (an output circuitry substrate). Specifically, as illustrated in FIGS. 3A to 3C, the first chip 21, the second chip 22, and the third chip 23 each have a plurality of functional devices described later arranged thereon and are formed such that the third chip 23, the second chip 22, and the first chip 21 are laminated in this order via a connection part 200.

The first chip 21 includes: a pixel unit 211 including a plurality of pixels that are arranged two-dimensionally in a matrix to receive light from outside and conduct photoelectric conversion so as to generate and output an imaging signal corresponding to the amount of received light; a column readout unit 212 that reads out an imaging signal stored in a pixel of the pixel unit 211; and a horizontal scanning unit 213 that outputs an imaging signal from a pixel of the pixel unit 211 in a horizontal direction. According to the first embodiment, the first chip 21 functions as an imager.

The second chip 22 includes a digital control oscillator 221, a timing control signal generator 222, and an A/D converter 223.

The digital control oscillator 221 is provided at the side of the distal end (the side of the proximal end of the imaging unit) of the transmission cable 3 to generate a drive clock signal (CLK) for driving the first chip 21 (imager) based on a phase digital signal input from a phase digital output unit 53 of the connector unit 5 described later via a signal line 34 of the transmission cable 3 and output the drive clock signal to the timing control signal generator 222.

The timing control signal generator 222 generates a drive signal for driving each unit of the first chip 21 (imager) and the imaging unit 20 based on a synchronization signal (SYNC) transmitted from a synchronization signal generator 63 of the processor 6 described later via a signal line 33 of the transmission cable 3 and a drive clock signal input from the digital control oscillator 221 and outputs the drive signal to each unit of the first chip 21 and the imaging unit 20. The timing control signal generator 222 includes a shift register unit 2221 that temporarily stores a synchronization signal transmitted from the synchronization signal generator 63 of the processor 6 described later via the signal line 33 of the transmission cable 3; a synchronization signal discriminator 2222 that discriminates the pattern of a synchronization signal stored in the shift register unit 2221; and a control signal generator 2223 that generates a drive signal based on a discrimination result from the synchronization signal discriminator 2222 and a reference clock signal input from the digital control oscillator 221 and outputs the drive signal to each unit of the first chip 21 and the imaging unit 20.

The A/D converter 223 performs A/D conversion processing on an analog imaging signal read from the horizontal scanning unit 213 to convert the analog imaging signal into a digital imaging signal and outputs the digital imaging signal to an output unit 231.

The third chip 23 includes the output unit 231 that outputs a digital imaging signal input from the A/D converter 223 via a signal line 35 of the transmission cable 3 to the connector unit 5; and a power source unit 232 including a capacitor, or the like, provided between the power supply voltage (VDD) and the ground (GND) transmitted via a signal line 31 and a signal line 32, respectively, of the transmission cable 3 to stabilize the power supply voltage transmitted to the imaging unit 20.

Configuration of the Transmission Cable

Next, a configuration of the transmission cable 3 is described.

The transmission cable 3 includes a plurality of signal lines. Specifically, the transmission cable 3 includes at least the signal line 31 for transmitting the power supply voltage, the signal line 32 for transmitting the ground, the signal line 33 for transmitting a synchronization signal, the signal line 34 for transmitting a phase digital signal, and the signal line 35 for transmitting an imaging signal. According to the first embodiment, the transmission cable 3 functions as a transmission path.

Configuration of the Connector Unit

Next, a configuration of the connector unit 5 is described.

The connector unit 5 includes a signal processing unit 51, a frequency divider 52, and a phase digital output unit 53.

The signal processing unit 51 performs predetermined signal processing on the imaging signal input from the imaging unit 20 via the signal line 35 of the transmission cable 3 and outputs it to the processor 6. Specifically, the signal processing unit 51 performs signal processing such as gain adjustment processing and format conversion processing on an imaging signal and outputs it to the processor 6. The signal processing unit 51 includes a field programmable gate array (FPGA) or the like.

The frequency divider 52 divides the frequency of a digital imaging signal, transmitted via the signal line 35 of the transmission cable 3, by an integer larger than one to convert (divide the frequency of) the imaging signal into a pulse signal and outputs the pulse signal to the phase digital output unit 53. For example, the frequency divider 52 decreases a digital imaging signal by ½ for conversion and outputs it to the phase digital output unit 53.

The phase digital output unit 53 is provided at the side of the end of the signal line 34 of the transmission cable 3. The phase digital output unit 53 generates a phase digital signal for controlling the oscillation frequency of the digital control oscillator 221 based on the phase difference between the digital imaging signal converted by the frequency divider 52 and the reference clock signal input from a reference clock signal generator 64 of the processor 6. The phase digital output unit 53 outputs a phase digital signal to the digital control oscillator 221 via the signal line 34 of the transmission cable 3. According to the first embodiment, the use of the phase digital output unit 53 and the digital control oscillator 221 via the transmission cable 3 forms a phase synchronization unit (PLL circuitry).

Configuration of the Processor

Next, a configuration of the processor 6 is described.

The processor 6 includes a power source 61, a clock generator 62, a synchronization signal generator 63, the reference clock signal generator 64, an image processing unit 65, and a control unit 66.

The power source 61 generates the power supply voltage (VDD) and outputs the generated power supply voltage together with the ground (GND) to the imaging unit 20 and the connector unit 5 via the signal line 31 and the signal line 32, respectively, of the transmission cable 3.

The clock generator 62 generates a clock signal that serves as a reference for the operation of each component of the endoscope system 1 and outputs the clock signal to the synchronization signal generator 63, the reference clock signal generator 64, and the control unit 66. The clock generator 62 includes a clock module.

The synchronization signal generator 63 generates a synchronization signal (SYNC) based on the clock signal input from the clock generator 62. The synchronization signal generator 63 outputs a synchronization signal to the timing control signal generator 222 of the imaging unit 20 via the signal line 33 of the transmission cable 3.

The reference clock signal generator 64 generates a reference clock signal based on the clock signal input from the clock generator 62 and outputs the reference clock signal to the phase digital output unit 53 of the connector unit 5.

The image processing unit 65 performs predetermined image processing on an imaging signal input from the signal processing unit 51 of the connector unit 5 and outputs it to the display device 7.

The control unit 66 integrally controls each unit of the endoscope system 1 in accordance with the timing of a clock signal input from the clock generator 62. The control unit 66 includes a central processing unit (CPU), a memory, or the like.

According to the above-described first embodiment, the use of the phase digital output unit 53 and the digital control oscillator 221 vie the transmission cable 3 forms a phase synchronization unit (PLL circuitry), whereby it is possible to reduce the diameter of the transmission cable 3.

Further, according to the first embodiment, as the phase digital output unit 53 outputs a phase digital signal to the digital control oscillator 221 via the signal line 34 of the transmission cable 3, it is possible to further reduce the diameter of the transmission cable 3 without considering the attenuation length due to the signal line 34.

According to the first embodiment, as the digital control oscillator 221 is provided in the imaging unit 20 at the side of the distal end 101 and a drive clock signal is generated by the imaging unit 20 at the side of the distal end 101, whereby high-precision drive clock signals may be generated without being affected by power supply dependency and temperature dependency.

According to the first embodiment, the phase digital output unit 53 is provided in the connector unit 5, and as the phase comparison is executed within the connector unit 5, it is possible to prevent the difference in the signal sampling timing due to the variation in the delay time by the transmission cable 3 and to enhance the resistance against disturbance noise.

According to the first embodiment, as the frequency divider 52 is provided in the connector unit 5, the frequency of an imaging signal may be adjusted to the target frequency even when the frequency is high.

According to the first embodiment, the frequency divider 52 and the phase digital output unit 53 are provided in the connector unit 5; however, the disclosure is not limited thereto, and the frequency divider 52 and the phase digital output unit 53 may be provided in the processor 6.

Figure 4A:
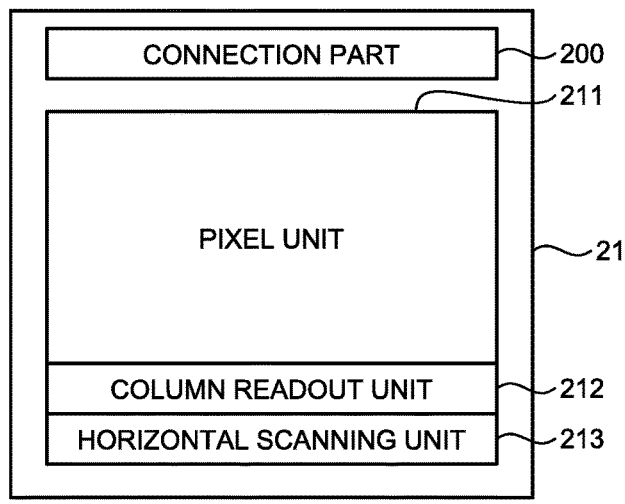
FIG. 4A is a plan view schematically illustrating another example of the arrangement of functional devices of the first chip according to the first embodiment.
Figure 4B:
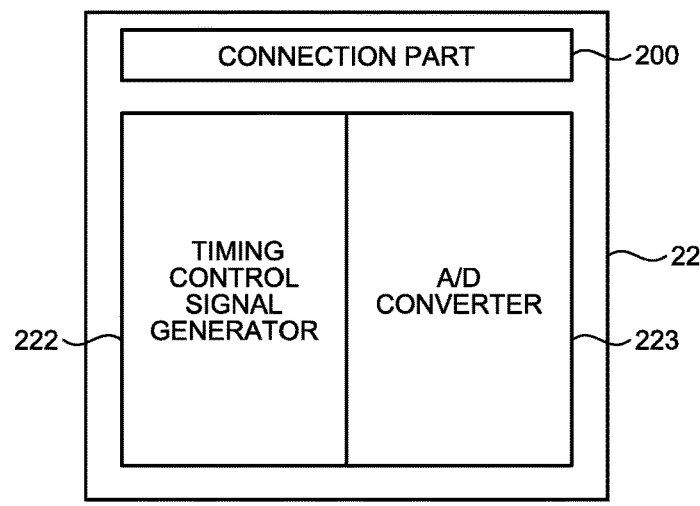
FIG. 4B is a plan view schematically illustrating another example of the arrangement of functional devices of the second chip according to the first embodiment.
Figure 4C:
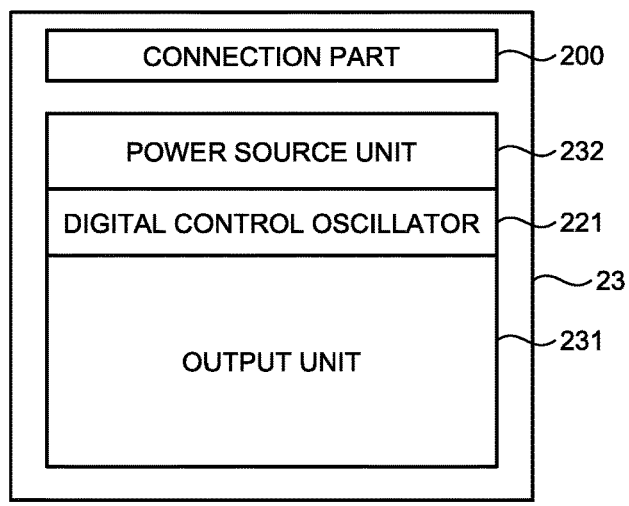
FIG. 4C is a plan view schematically illustrating another example of the arrangement of functional devices of the third chip according to the first embodiment.

According to the first embodiment, the functional devices provided in the first chip 21, the second chip 22, and the third chip 23 may be changed as appropriate. Specifically, as illustrated in FIGS. 4A, 4B, and 4C, the digital control oscillator 221 may be provided in the third chip 23 instead of the second chip 22.

Second Embodiment

Next, a second embodiment is described. According to the above-described first embodiment, a phase digital signal is transmitted to the imaging unit 20 via the signal line 34 of the transmission cable 3; however, according to the second embodiment, a phase digital signal is transmitted to an imaging unit in a superimposed manner via the signal line of a transmission cable for transmitting a synchronization signal. A configuration of an endoscope system 1a according to the second embodiment is described below. The same component as that in the above-described first embodiment is denoted by the same reference numeral, and descriptions thereof are omitted.

Configuration of the Relevant Part of the Endoscope System

Figure 5:
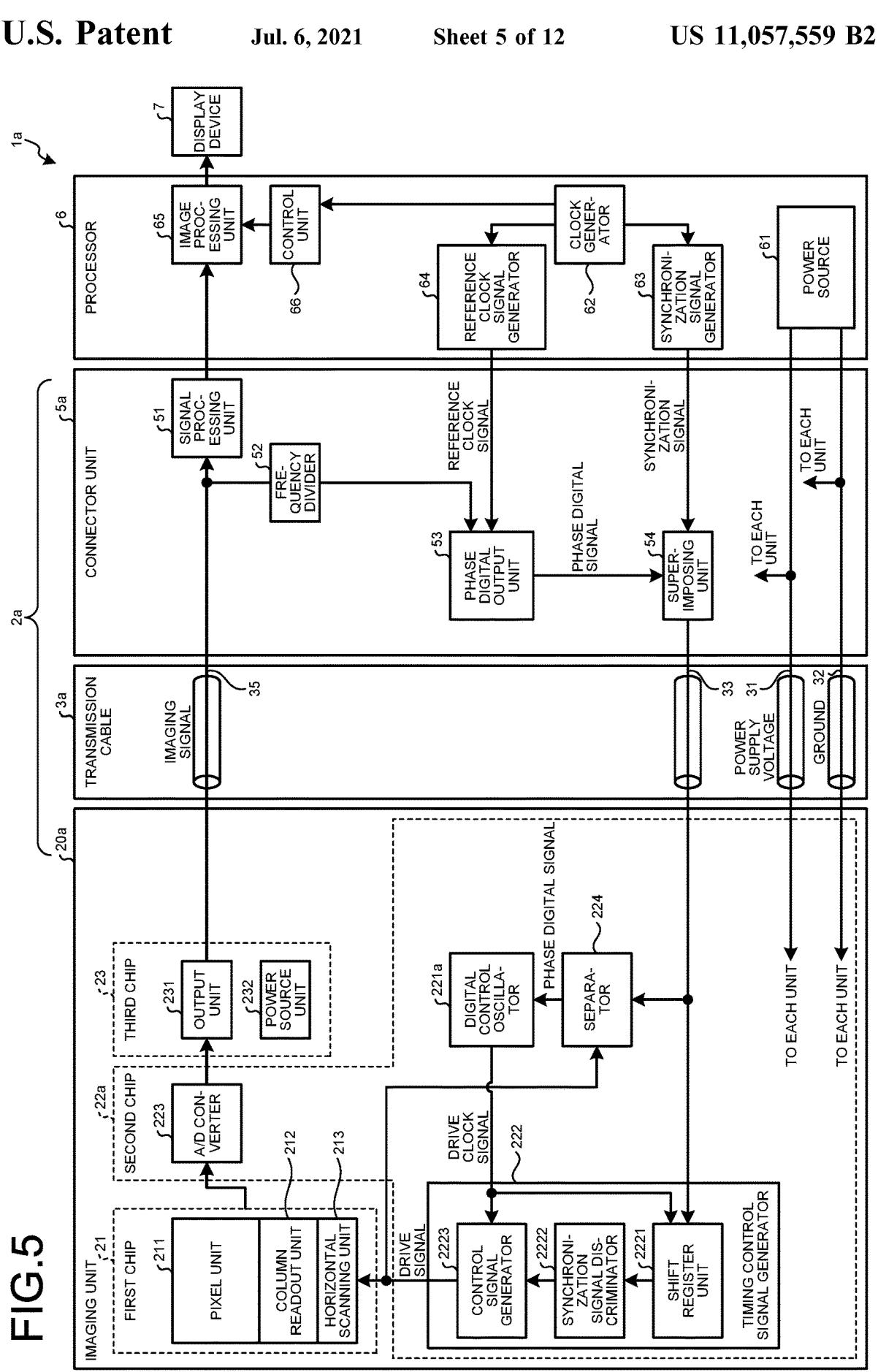
FIG. 5 is a block diagram illustrating a functional configuration of the relevant part of an endoscope system according to a second embodiment.

FIG. 5 is a block diagram illustrating a functional configuration of the relevant part of the endoscope system 1a according to the second embodiment. The endoscope system 1a illustrated in FIG. 5 includes an endoscope 2a instead of the endoscope 2 according to the above-described first embodiment. The endoscope 2a includes an imaging unit 20a, a transmission cable 3a, and a connector unit 5a instead of the imaging unit 20, the transmission cable 3, and the connector unit 5 according to the above-described first embodiment.

Configuration of the Imaging Unit First, a configuration of the imaging unit 20a is described.

As illustrated in FIG. 5, the imaging unit 20a includes a second chip 22a instead of the second chip 22 according to the above-described first embodiment. The second chip 22a includes a digital control oscillator 221a, the timing control signal generator 222, the A/D converter 223, and a separator 224.

The digital control oscillator 221a generates a drive clock signal (CLK) for driving the imaging unit 20a based on a phase digital signal separated by the separator 224 described later and outputs the drive clock signal to the timing control signal generator 222.

Based on a drive signal input from the timing control signal generator 222, the separator 224 separates, from a synchronization signal, the phase digital signal transmitted from a superimposing unit 54 of the connector unit 5a described later in a time-division manner via the signal line 33 of the transmission cable 3a and outputs the phase digital signal to the digital control oscillator 221a.

Configuration of the Transmission Cable

Next, a configuration of the transmission cable 3a is described.

As illustrated in FIG. 5, the transmission cable 3a includes the signal line 31, the signal line 32, the signal line 33, and the signal line 35.

Configuration of the Connector Unit

Next, a configuration of the connector unit 5a is described.

As illustrated in FIG. 5, the connector unit 5a further includes the superimposing unit 54 in addition to the components of the connector unit 5 according to the above-described first embodiment.

The superimposing unit 54 outputs a phase digital signal input from the phase digital output unit 53 and a synchronization signal input from the synchronization signal generator 63 to the timing control signal generator 222 and the separator 224 in a time-division manner via the signal line 33 of the transmission cable 3a. Specifically, the superimposing unit 54 outputs, as a synchronization signal, a vertical synchronization signal of one pattern during a vertical transfer period and outputs a horizontal synchronization signal of one pulse during a horizontal transfer period and also outputs a phase digital signal with a predetermined voltage in a superimposed manner in a period other than the vertical transfer period and the horizontal transfer period.

According to the above-described second embodiment, the superimposing unit 54 outputs a phase digital signal input from the phase digital output unit 53 and a synchronization signal input from the synchronization signal generator 63 to the timing control signal generator 222 and the separator 224 in a time-division manner via the signal line 33 of the transmission cable 3a, whereby it is possible to reduce the number of signal lines as compared with the above-described first embodiment so as to further reduce the diameter of the transmission cable 3a.

Third Embodiment

Next, a third embodiment is described. According to the third embodiment, a phase digital signal and an imaging signal are transmitted via the signal line for transmitting the imaging signal in a time-division manner. A configuration of an endoscope system 1b according to the third embodiment is described below. The same component as that in the above-described first embodiment is denoted by the same reference numeral, and descriptions thereof are omitted.

Configuration of the Relevant Part of the Endoscope System

Figure 6:
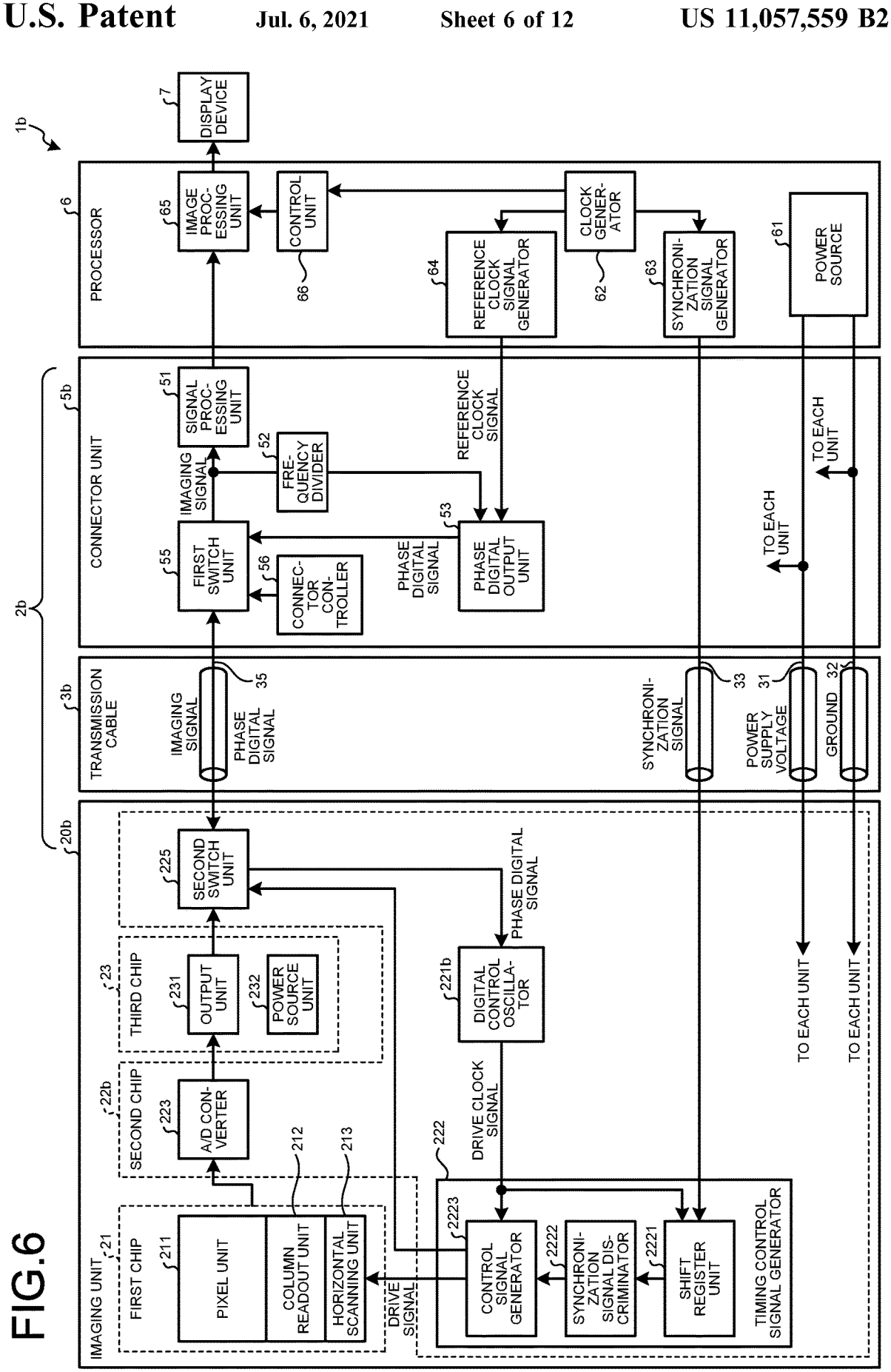
FIG. 6 is a block diagram illustrating a functional configuration of the relevant part of an endoscope system according to a third embodiment.

FIG. 6 is a block diagram illustrating a functional configuration of the relevant part of the endoscope system 1b according to the third embodiment. The endoscope system 1b illustrated in FIG. 6 includes an endoscope 2b instead of the endoscope 2 according to the above-described first embodiment. The endoscope 2b includes an imaging unit 20b, a transmission cable 3b, and a connector unit 5b instead of the imaging unit 20, the transmission cable 3, and the connector unit 5 according to the above-described first embodiment.

Configuration of the Imaging Unit

First, a configuration of the imaging unit 20b is described.

As illustrated in FIG. 6, the imaging unit 20b includes a second chip 22b instead of the second chip 22 according to the above-described first embodiment. The second chip 22b includes a digital control oscillator 221b, the timing control signal generator 222, the A/D converter 223, and a second switch unit 225.

The digital control oscillator 221b generates a drive clock signal (CLK) for driving the imaging unit 20b based on a phase digital signal input from the second switch unit 225 described later and outputs the drive clock signal to the timing control signal generator 222.

Under the control of the timing control signal generator 222, the second switch unit 225 connects the output unit 231 to the signal line 35 of the transmission cable 3b and connects the digital control oscillator 221b to the signal line 35 of the transmission cable 3b. The second switch unit 225 includes a semiconductor switch, a multiplexer, a physical switch, or the like.

In the imaging unit 20b having the above configuration, the timing control signal generator 222 causes the second switch unit 225 to connect the signal line 35 to the output unit 231 in an imaging signal transmission period and causes the second switch unit 225 to connect the signal line 35 to the digital control oscillator 221b in a period other than the imaging signal transmission period.

Configuration of the Transmission Cable

Next, a configuration of the transmission cable 3b is described.

As illustrated in FIG. 6, the transmission cable 3b includes the signal line 31, the signal line 32, the signal line 33, and the signal line 35. The distal end side of the signal line 35 is connected to the second switch unit 225, and the proximal end side thereof is connected to a first switch unit 55.

Configuration of the Connector Unit

Next, a configuration of the connector unit 5b is described.

As illustrated in FIG. 6, the connector unit 5b further includes the first switch unit 55 and a connector controller 56 in addition to the components of the connector unit 5 according to the above-described first embodiment.

Under the control of the connector controller 56, the first switch unit 55 connects the signal line 35 to the signal processing unit 51 and connects the signal line 35 to the phase digital output unit 53. The first switch unit 55 includes a semiconductor switch, a multiplexer, a physical switch, or the like.

The connector controller 56 controls the driving of the first switch unit 55. Specifically, the connector controller 56 causes the signal line 35 and the signal processing unit 51 to be connected in the imaging signal transmission period and causes the signal line 35 and the phase digital output unit 53 to be connected in a period other than the imaging signal transmission period. The connector controller 56 includes an FPGA, or the like.

According to the above-described third embodiment, a phase digital signal is transmitted via the signal line 35 of the transmission cable 3b in a time-division manner, whereby it is possible to reduce the number of signal lines as compared with the above-described first embodiment so as to further reduce the diameter of the transmission cable 3b.

Fourth Embodiment

Next, a fourth embodiment is described. According to the fourth embodiment, a phase digital signal is transmitted to an imaging unit in a superimposed manner with the power supply voltage. A configuration of an endoscope system 1c according to the fourth embodiment is described below. The same component as that in the above-described first embodiment is denoted by the same reference numeral, and descriptions thereof are omitted.

Configuration of the Relevant Part of the Endoscope System

Figure 7:
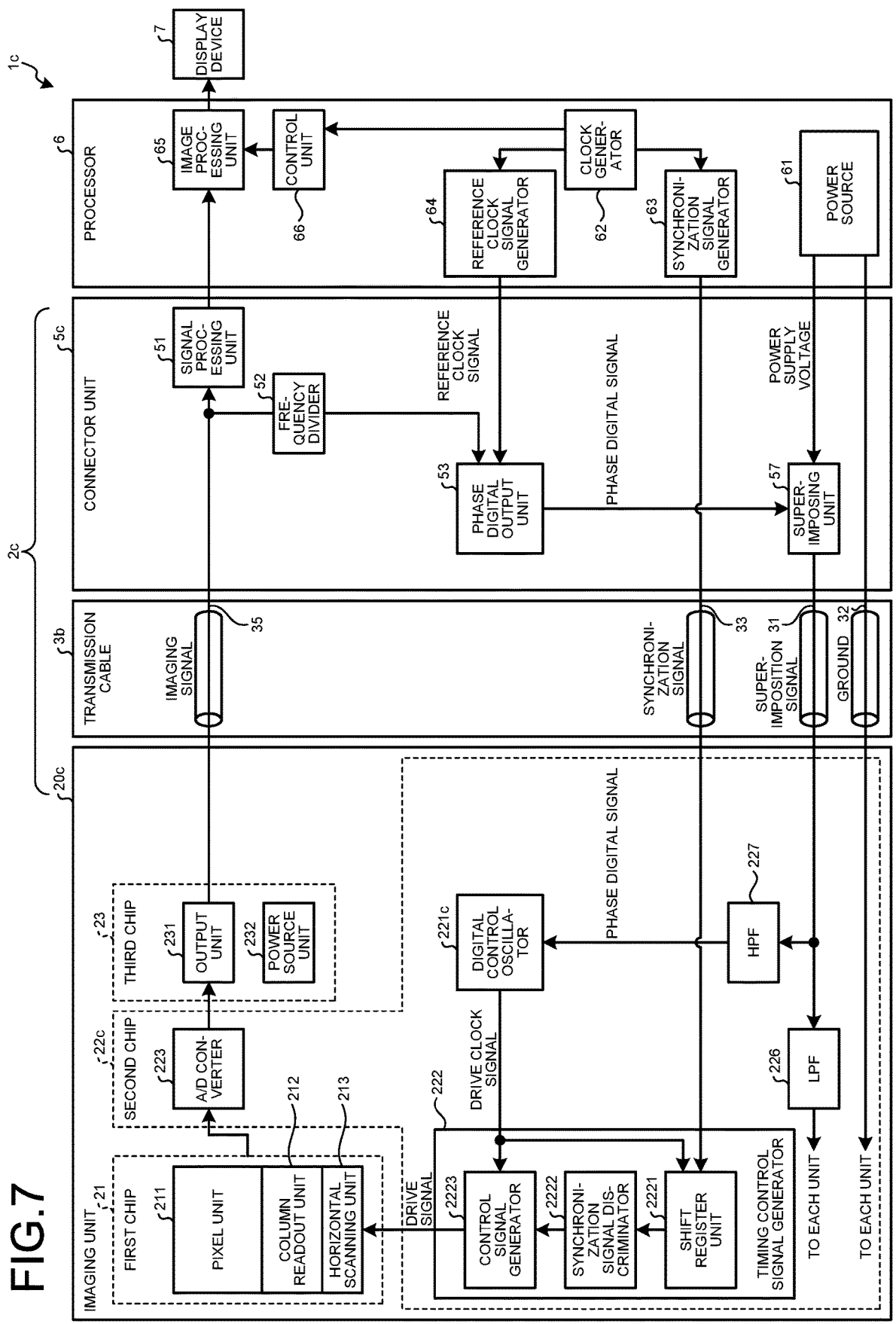
FIG. 7 is a block diagram illustrating a functional configuration of the relevant part of an endoscope system according to a fourth embodiment.

FIG. 7 is a block diagram illustrating a functional configuration of the relevant part of the endoscope system 1c according to the fourth embodiment. The endoscope system 1c illustrated in FIG. 7 includes an endoscope 2c instead of the endoscope 2 according to the above-described first embodiment. The endoscope 2c includes an imaging unit 20c, the transmission cable 3b according to the above-described third embodiment, and a connector unit 5c instead of the imaging unit 20, the transmission cable 3, and the connector unit 5 according to the above-described first embodiment.

Configuration of the Imaging Unit

First, a configuration of the imaging unit 20c is described.

As illustrated in FIG. 7, the imaging unit 20c includes a second chip 22c instead of the second chip 22 according to the above-described first embodiment. The second chip 22c includes a digital control oscillator 221c, the timing control signal generator 222, the A/D converter 223, a low pass filter (LPF) 226, and a high pass filter (HPF) 227.

The digital control oscillator 221c generates a drive clock signal (CLK) for driving the imaging unit 20c based on a phase digital signal extracted from a superimposition signal by the HPF 227 described later and outputs the drive clock signal to the timing control signal generator 222.

The LPF 226 removes the phase digital signal from the superimposition signal transmitted via the signal line 31 of the transmission cable 3b to obtain the power supply voltage and outputs the power supply voltage to each unit of the imaging unit 20c.

The HPF 227 extracts a phase digital signal from the superimposition signal transmitted via the signal line 31 of the transmission cable 3b and outputs the phase digital signal to the digital control oscillator 221c. According to the fourth embodiment, the HPF 227 functions as an extracting unit.

Configuration of the Connector Unit

Next, a configuration of the connector unit 5c is described.

As illustrated in FIG. 7, the connector unit 5c further includes a superimposing unit 57 in addition to the components of the connector unit 5 according to the above-described first embodiment.

The superimposing unit 57 superimposes the phase digital signal input from the phase digital output unit 53 onto the power supply voltage input from the power source 61 and outputs it to the signal line 31. In a case where there are multiple power supply voltages from the power source 61, the superimposing unit 57 may superimpose a phase digital signal onto any one or more of the signal lines for transmitting the respective power supply voltages and output it.

According to the above-described fourth embodiment, the superimposition signal in which the phase digital signal is superimposed on the power supply voltage is transmitted via the signal line 31 of the transmission cable 3b, whereby it is possible to reduce the number of signal lines as compared with the above-described first embodiment so as to further reduce the diameter of the transmission cable 3b.

Fifth Embodiment

Next, a fifth embodiment is described. According to the fifth embodiment, a superimposition signal in which a phase digital signal and a synchronization signal are superimposed is transmitted via the signal line for transmitting an imaging signal in a time-division manner. A configuration of an endoscope system 1d according to the fifth embodiment is described below. The same component as that in the above-described first embodiment is denoted by the same reference numeral, and descriptions thereof are omitted.

Configuration of the Relevant Part of the Endoscope System

Figure 8:
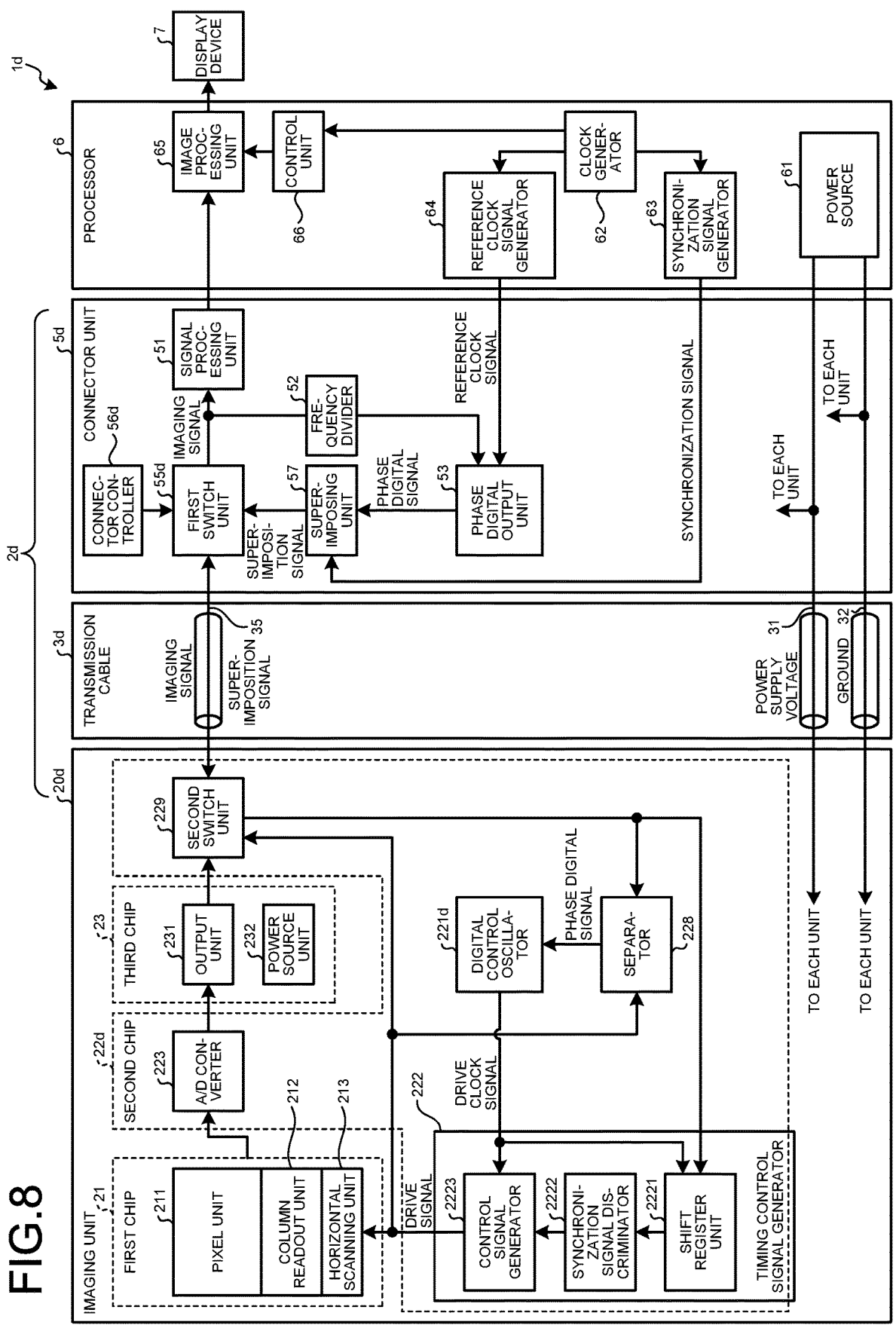
FIG. 8 is a block diagram illustrating a functional configuration of the relevant part of an endoscope system according to a fifth embodiment.

FIG. 8 is a block diagram illustrating a functional configuration of the relevant part of the endoscope system 1d according to the fifth embodiment. The endoscope system 1d illustrated in FIG. 8 includes an endoscope 2d instead of the endoscope 2 according to the above-described first embodiment. The endoscope 2d includes an imaging unit 20d, a transmission cable 3d, and a connector unit 5d instead of the imaging unit 20, the transmission cable 3, and the connector unit 5 according to the above-described first embodiment.

Configuration of the Imaging Unit

First, a configuration of the imaging unit 20d is described.

As illustrated in FIG. 8, the imaging unit 20d includes a second chip 22d instead of the second chip 22 according to the above-described first embodiment. The second chip 22d includes a digital control oscillator 221d, the timing control signal generator 222, a separator 228, and a second switch unit 229.

The digital control oscillator 221d generates a drive clock signal (CLK) for driving the imaging unit 20d based on a phase digital signal separated from a superimposition signal by the separator 228 described later and outputs the drive clock signal to the timing control signal generator 222.

Under the control of the timing control signal generator 222, the separator 228 separates the phase digital signal from the superimposition signal (the signal in which the phase digital signal is superimposed on the synchronization signal) transmitted via the second switch unit 229 in a time-division manner during the period in which the phase digital signal is superimposed and outputs the phase digital signal to the digital control oscillator 221d.

Under the control of the timing control signal generator 222, the second switch unit 229 connects the output unit 231 to the signal line 35 of the transmission cable 3d and connects the signal line 35 of the transmission cable 3d to the separator 228 and the timing control signal generator 222. The second switch unit 229 includes a semiconductor switch, a multiplexer, a physical switch, or the like.

In the imaging unit 20d having the above configuration, the timing control signal generator 222 causes the second switch unit 229 to connect the signal line 35 to the output unit 231 in the imaging signal transmission period and causes the second switch unit 229 to connect the signal line 35 to the separator 228 and the timing control signal generator 222 in a period other than the imaging signal transmission period.

Configuration of the Transmission Cable

Next, a configuration of the transmission cable 3d is described.

As illustrated in FIG. 8, the transmission cable 3d includes the signal line 31, the signal line 32, and the signal line 35.

Configuration of the Connector Unit

Next, a configuration of the connector unit 5d is described.

As illustrated in FIG. 8, the connector unit 5d includes a first switch unit 55d, a connector controller 56d, and the superimposing unit 57 in addition to the components of the connector unit 5 according to the above-described first embodiment.

Under the control of the connector controller 56d, the first switch unit 55d connects the signal line 35 to the signal processing unit 51 and connects the signal line 35 to the superimposing unit 57. The first switch unit 55d includes a semiconductor switch, a multiplexer, a physical switch, or the like.

The connector controller 56d controls the driving of the first switch unit 55d. Specifically, the connector controller 56d connects the signal line 35 to the signal processing unit 51 in the imaging signal transmission period and connects the signal line 35 to the superimposing unit 57 in a period other than the imaging signal transmission period. The connector controller 56d includes an FPGA, or the like.

The superimposing unit 57 outputs a phase digital signal input from the phase digital output unit 53 and a synchronization signal input from the synchronization signal generator 63 to the signal line 35 of the transmission cable 3d via the first switch unit 55d.

According to the above-described fifth embodiment, a superimposition signal in which a phase digital signal is superimposed on a synchronization signal is transmitted to the signal line 35 of the transmission cable 3b in a time-division manner, whereby it is possible to reduce the number of signal lines as compared with the above-described first embodiment so as to further reduce the diameter of the transmission cable 3d.

Sixth Embodiment

Next, a sixth embodiment is described. According to the sixth embodiment, the external noise generated due to the use of a treatment tool such as an electric cautery is eliminated. A configuration of an endoscope system according to the sixth embodiment is described below. The same component as that in the above-described first embodiment is denoted by the same reference numeral, and descriptions thereof are omitted.

Configuration of the Relevant Part of the Endoscope System

Figure 9:
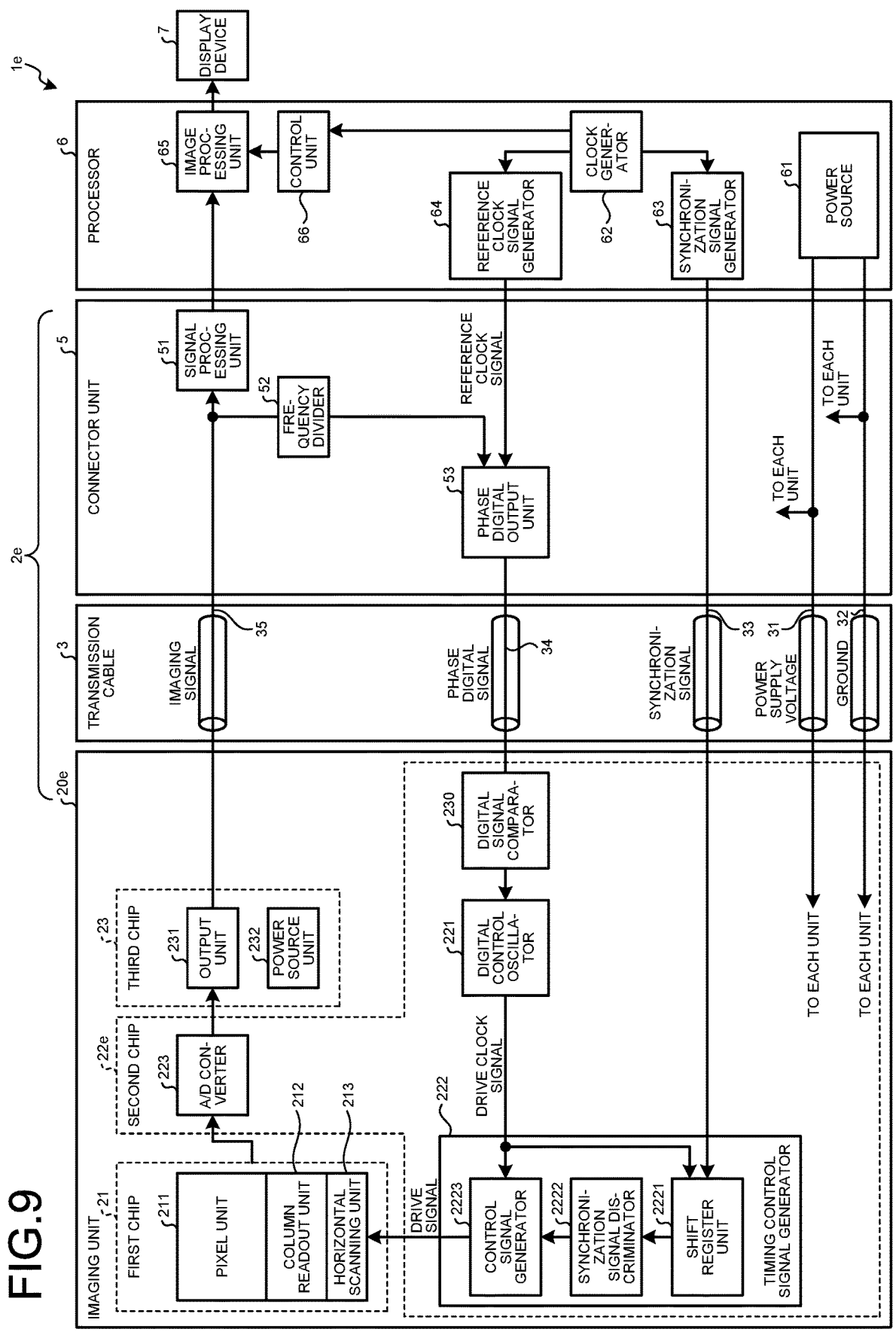
FIG. 9 is a block diagram illustrating a functional configuration of the relevant part of an endoscope system according to a sixth embodiment.

FIG. 9 is a block diagram illustrating a functional configuration of the relevant part of an endoscope system 1e according to the sixth embodiment. The endoscope system 1e illustrated in FIG. 9 includes an endoscope 2e instead of the endoscope 2 according to the above-described first embodiment. The endoscope 2e includes an imaging unit 20e instead of the imaging unit 20 according to the above-described first embodiment.

Configuration of the Imaging Unit

A configuration of the imaging unit 20e is described.

As illustrated in FIG. 9, the imaging unit 20e includes a second chip 22e instead of the second chip 22 according to the above-described first embodiment. The second chip 22e further includes a digital signal comparator 230 in addition to the components of the second chip 22 according to the above-described first embodiment.

The digital signal comparator 230 calculates the difference between the digital value of the phase digital signal transmitted from the phase digital output unit 53 via the signal line 34 and the digital value of the previous phase digital signal by a predetermined time. The digital signal comparator 230 also determines whether a calculation result is more than a threshold. When the calculation result is more than the threshold, the digital signal comparator 230 outputs the digital value of the previous phase digital signal by a predetermined time to the digital control oscillator 221. When the calculation result is not more than the threshold, the digital signal comparator 230 outputs the digital value of the phase digital signal transmitted from the phase digital output unit 53 via the signal line 34 to the digital control oscillator 221. According to the sixth embodiment, the digital signal comparator 230 functions as a noise remover that removes noise of a phase digital signal.

According to the above-described sixth embodiment, as the digital signal comparator 230 is provided in the imaging unit 20$e$, it is possible to prevent the effect of external noise when a treatment tool that generates a high frequency, such as an electric cautery, is used.

Seventh Embodiment

Next, a seventh embodiment is described. According to the seventh embodiment, the external noise generated due to the use of a treatment tool such as an electric cautery is removed. A configuration of an endoscope system if according to the seventh embodiment is described below. The same component as that in the above-described first embodiment is denoted by the same reference numeral, and descriptions thereof are omitted.

Configuration of the Relevant Part of the Endoscope System

Figure 10:
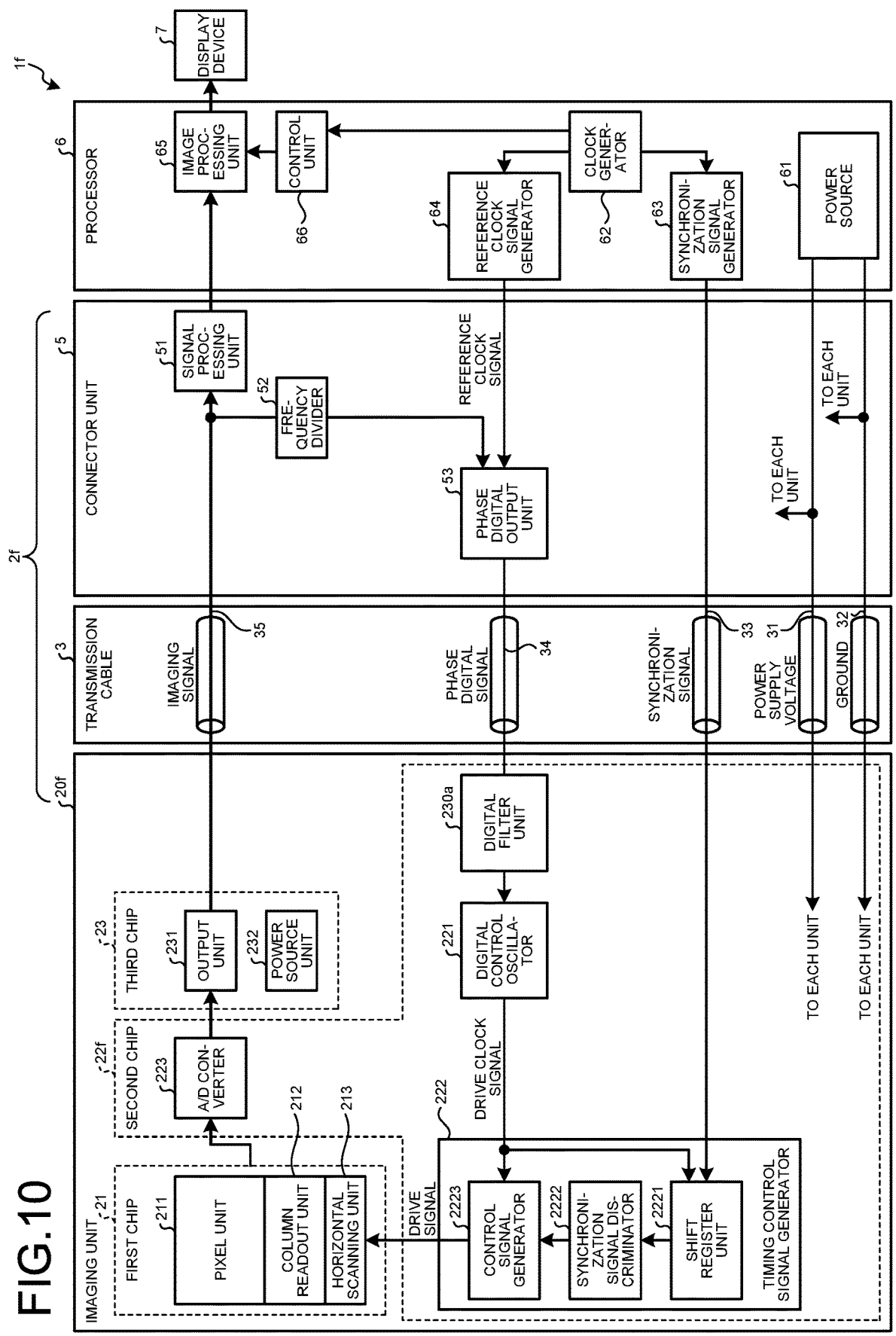
FIG. 10 is a block diagram illustrating a functional configuration of the relevant part of an endoscope system according to a seventh embodiment.

FIG. 10 is a block diagram illustrating a functional configuration of the relevant part of the endoscope system if according to the seventh embodiment. The endoscope system if illustrated in FIG. 10 includes an endoscope 2$f$ instead of the endoscope 2 according to the above-described first embodiment. The endoscope 2$f$ includes an imaging unit 20$f$ instead of the imaging unit 20 according to the above-described first embodiment.

Configuration of the Imaging Unit

A configuration of the imaging unit 20$f$ is described.

As illustrated in FIG. 10, the imaging unit 20$f$ includes a second chip 22$f$ instead of the second chip 22 according to the above-described first embodiment. The second chip 22$f$ further includes a digital filter unit 230$a$ in addition to the components of the second chip 22 according to the above-described first embodiment. According to the seventh embodiment, the digital filter unit 230$a$ functions as a noise remover that removes noise of a phase digital signal.

The digital filter unit 230$a$ includes, for example, a low-pass filter that sequentially adds the digital value of a phase digital signal transmitted from the phase digital output unit 53 via the signal line 34, divides the sum by the number of the added digital values, and outputs the obtained digital value.

According to the above-described seventh embodiment, as the digital filter unit 230$a$ is provided in the imaging unit 20$f$, it is possible to prevent the effect of external noise when a treatment tool that generates a high frequency, such as an electric cautery, is used.

Eighth Embodiment

Next, an eighth embodiment is described. According to the eighth embodiment, the external noise generated due to the use of a treatment tool such as an electric cautery is removed. A configuration of an endoscope system 1$g$ according to the eighth embodiment is described below. The same component as that in the above-described first embodiment is denoted by the same reference numeral, and descriptions thereof are omitted.

Configuration of the Relevant Part of the Endoscope System

Figure 11:
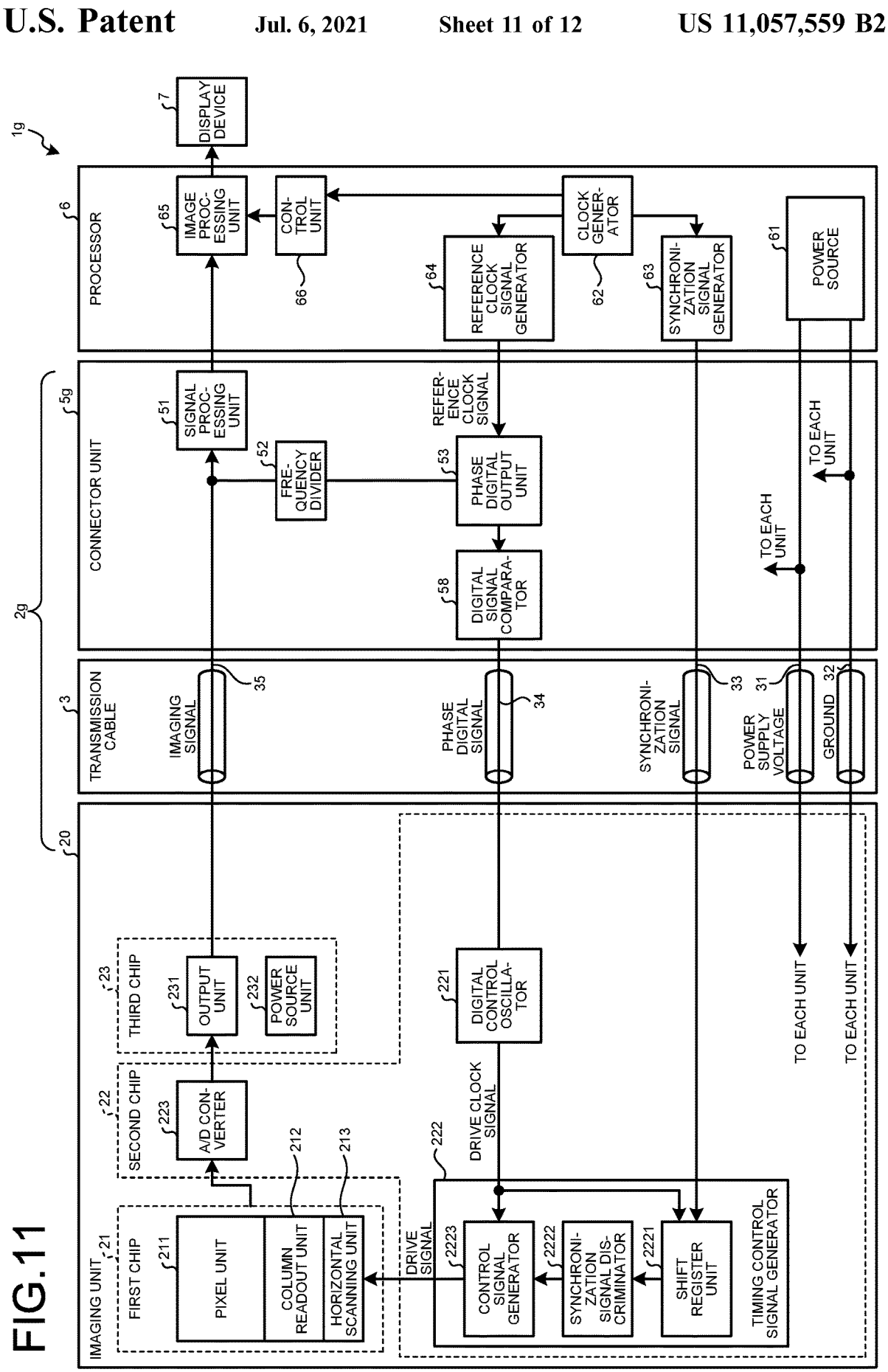
FIG. 11 is a block diagram illustrating a functional configuration of the relevant part of an endoscope system according to an eighth embodiment.

FIG. 11 is a block diagram illustrating a functional configuration of the relevant part of the endoscope system 1$g$ according to the eighth embodiment. The endoscope system 1$g$ illustrated in FIG. 11 includes an endoscope 2$g$ instead of the endoscope 2 according to the above-described first embodiment. The endoscope 2$g$ includes a connector unit 5$g$ instead of the connector unit 5 according to the above-described first embodiment.

Configuration of the Connector Unit

A configuration of the connector unit 5$g$ is described.

As illustrated in FIG. 11, the connector unit 5$g$ further includes a digital signal comparator 58 in addition to the components of the connector unit 5 according to the above-described first embodiment.

The digital signal comparator 58 calculates the difference between the digital value of the phase digital signal input from the phase digital output unit 53 and the digital value of the previous phase digital signal by a predetermined time and also determines whether the calculation result is more than a threshold. When the calculation result is more than the threshold, the digital signal comparator 58 outputs the digital value of the previous phase digital signal by the predetermined time to the digital control oscillator 221 via the signal line 34. When the calculation result is not more than the threshold, the digital signal comparator 58 outputs the digital value of the phase digital signal input from the phase digital output unit 53 to the digital control oscillator 221 via the signal line 34. According to the eighth embodiment, the digital signal comparator 58 functions as a noise remover that removes noise of a phase digital signal.

According to the above-described eighth embodiment, as the digital signal comparator 58 is provided in the connector unit 5$g$, it is possible to prevent the effect of external noise when a treatment tool that generates a high frequency, such as an electric cautery, is used.

Ninth Embodiment

Next, a ninth embodiment is described. According to the ninth embodiment, the external noise generated due to the use of a treatment tool such as an electric cautery is removed. A configuration of an endoscope system 1$h$ according to the ninth embodiment is described below. The same component as that in the above-described first embodiment is denoted by the same reference numeral, and descriptions thereof are omitted.

Configuration of the Relevant Part of the Endoscope System

Figure 12:
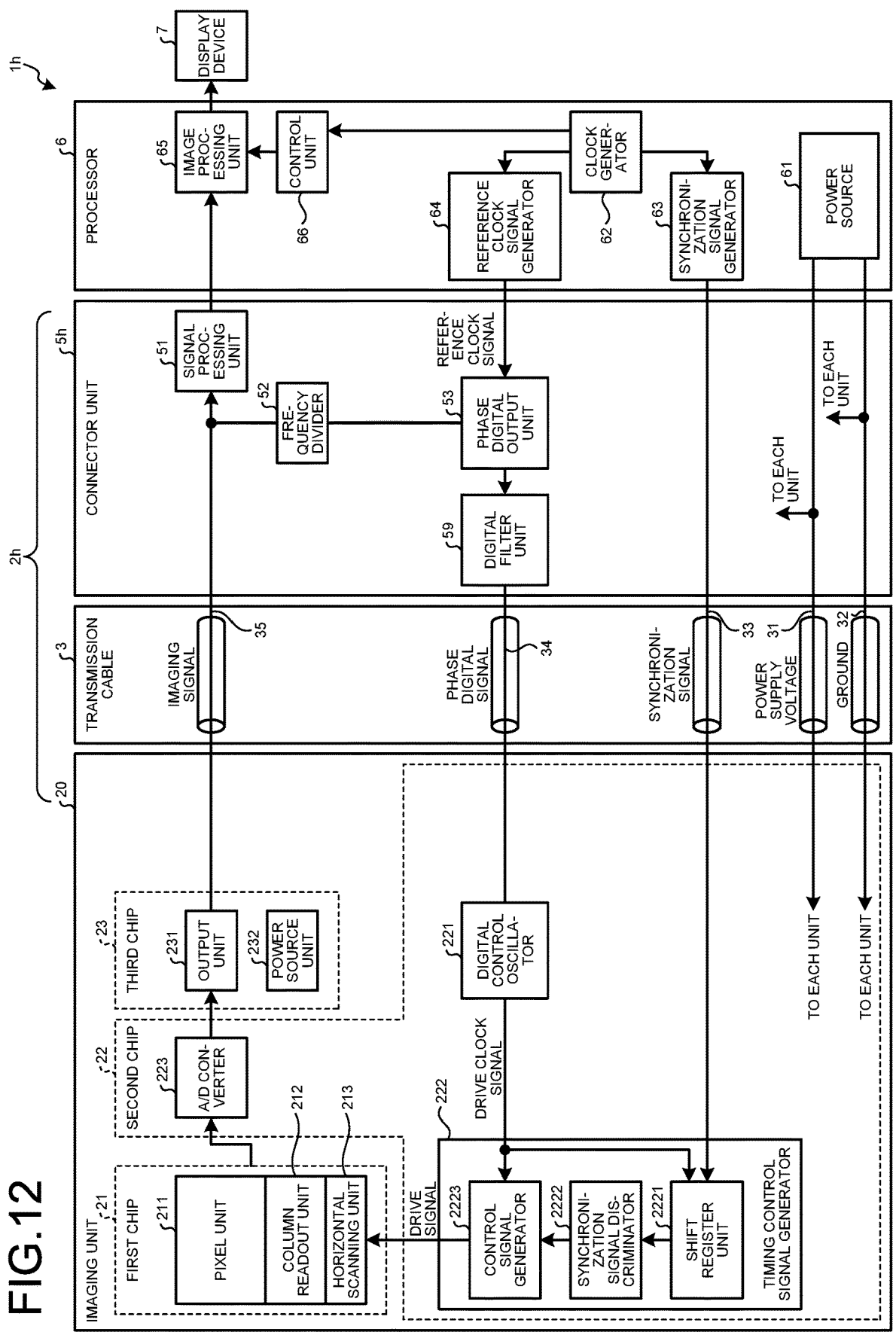
FIG. 12 is a block diagram illustrating a functional configuration of the relevant part of an endoscope system according to a ninth embodiment.

FIG. 12 is a block diagram illustrating a functional configuration of the relevant part of the endoscope system 1$h$ according to the ninth embodiment. The endoscope system 1$h$ illustrated in FIG. 12 includes an endoscope 2$h$ instead of the endoscope 2 according to the above-described first embodiment. The endoscope 2$h$ includes a connector unit 5$h$ instead of the connector unit 5 according to the above-described first embodiment.

Configuration of the Connector Unit

A configuration of the connector unit 5$h$ is described.

As illustrated in FIG. 12, the connector unit 5h further includes a digital filter unit 59 in addition to the components of the connector unit 5 according to the above-described first embodiment.

The digital filter unit 59, for example, sequentially adds the digital value of a phase digital signal input from the phase digital output unit 53, divides the sum by the number of the added digital values, and outputs the obtained digital value to the digital control oscillator 221. According to the ninth embodiment, the digital filter unit 59 functions as a noise remover that removes noise of a phase digital signal.

According to the above-described ninth embodiment, as the digital filter unit 59 is provided in the connector unit 5h, it is possible to prevent the effect of external noise when a treatment tool that generates a high frequency, such as an electric cautery, is used.

Other Embodiments

The components disclosed in the first embodiment to the ninth embodiment described above may be combined as appropriate to form various embodiments. For example, some components may be deleted from all the components described in the first embodiment to the ninth embodiment described above. Furthermore, the components described in the first embodiment to the ninth embodiment described above may be combined as appropriate.

According to the first embodiment to the ninth embodiment, the control device and the light source device are separately provided; however, the control device and the light source device may be integrally formed.

In the first embodiment to the ninth embodiment, the above-described "unit" may be interpreted as "means", "circuitry", etc. For example, the control unit may be interpreted as a control means or control circuitry.

In the first embodiment to the ninth embodiment, the endoscope system is applied; however, for example, a capsule endoscope, a video microscope that captures an object, a cell phone having an imaging function, or a tablet terminal having an imaging function is also applicable.

According to the disclosure, there is an advantage such that it is possible to further reduce the diameter of a transmission cable.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an imaging circuit configured to execute photoelectric conversion on received light to generate an imaging signal;
   a transmission cable configured to connect the imaging circuit to a control device configured to perform image processing on the imaging signal generated by the imaging circuit so as to transmit the imaging signal;
   a phase synchronization unit including:
      a digital control oscillator that is provided at a side of a distal end of the transmission cable, the digital control oscillator being configured to generate a drive clock signal that drives the imaging circuit; and
      a phase digital output circuit that is provided in a connector unit and at a side of a proximal end of the transmission cable, the phase digital output circuit being configured to generate a phase digital signal that controls an oscillation frequency of the drive clock signal generated by the digital control oscillator, which is located in the imaging unit at the side of the distal end of the transmission cable, the phase digital signal being generated based on a phase difference between a reference clock signal and the imaging signal, which has a frequency divided prior to generating the phase digital signal, and the phase digital output circuit is configured to output the generated phase digital signal to the digital control oscillator via the transmission cable;
   a first switch that is provided at the side of the proximal end of the transmission cable, the first switch being configured to connect the transmission cable to one of the control device and the phase digital output circuit;
   a control unit configured to:
      cause the first switch to connect the transmission cable to the control device in an imaging signal transmission time period for transmitting the imaging signal, and
      cause the first switch to connect the transmission cable to the phase digital output circuit in a time period other than the imaging signal transmission time period;
   a second switch that is provided at the side of the distal end of the transmission cable, the second switch being configured to connect the transmission cable to one of the imaging circuit and the digital control oscillator; and
   a timing control signal generating circuit configured to:
      cause the second switch to connect the transmission cable to the imaging circuit in the imaging signal transmission time period, and
      cause the second switch to connect the transmission cable to the digital control oscillator in the time period other than the imaging signal transmission time period.

2. The endoscope according to claim 1, wherein the phase synchronization unit further includes a noise removing filter configured to filter the phase digital signal to remove noise of the phase digital signal.

3. The endoscope according to claim 1, wherein the phase synchronization unit further includes a frequency divider configured to divide a frequency of the imaging signal by an integer value, which is larger than one, to convert the imaging signal into a pulse signal, the frequency divider being configured to output the pulse signal to the phase digital output circuit.

4. The endoscope according to claim 1, further comprising:
   an insertion part configured to be inserted into a subject, the insertion part including the digital control oscillator; and
   a connector removably connected to the control device, the connector including the phase digital output circuit.

5. An endoscope system comprising:
   an endoscope including:
      an imaging circuit configured to execute photoelectric conversion on received light to generate an imaging signal; and
      an insertion part configured to be inserted into a subject, the insertion part including the imaging circuit at a distal end portion of the insertion part;
   a timing control signal generating circuit configured to generate a drive signal to drive the imaging circuit;

a control device configured to perform image processing on the imaging signal generated by the imaging circuit;

a transmission cable configured to connect the imaging circuit to the control device to transmit the generated imaging signal;

a phase synchronization unit including:
  a digital control oscillator that is provided at a side of a distal end of the transmission cable, the digital control oscillator being configured to generate a drive clock signal for the timing control signal generating circuit to generate the drive signal; and
  a phase digital output circuit that is provided in a connector unit and at a side of a proximal end of the transmission cable, the phase digital output circuit being configured to generate a phase digital signal that controls an oscillation frequency of the drive clock signal generated by the digital control oscillator, which is located in the imaging unit at the side of the distal end of the transmission cable, the phase digital signal being generated based on a phase difference between a reference clock signal and the imaging signal, which has a frequency divided prior to generating the phase digital signal, the phase digital output circuit being configured to output the phase digital signal to the digital control oscillator via the transmission cable;

a first switch that is provided at the side of the proximal end of the transmission cable, the first switch being configured to connect the transmission cable to one of the control device and the phase digital output circuit;

a control unit configured to:
  cause the first switch to connect the transmission cable to the control device in an imaging signal transmission time period for transmitting the imaging signal, and
  cause the first switch to connect the transmission cable to the phase digital output circuit in a time period other than the imaging signal transmission time period; and
  a second switch that is provided at the side of the distal end of the transmission cable, the second switch being configured to connect the transmission cable to one of the imaging circuit and the digital control oscillator, the timing control signal generating circuit causing the second switch to connect the transmission cable to the imaging circuit in the imaging signal transmission time period, and the timing control signal generating circuit causing the second switch to connect the transmission cable to the digital control oscillator in the time period other than the imaging signal transmission time period.

6. The endoscope according to claim 1, further comprising a superimposing circuit that (i) generates and outputs a vertical synchronization signal of one pattern during a vertical transfer period and a horizontal synchronization signal of one pulse during a horizontal transfer period, and (ii) generates and outputs a phase digital signal with a predetermined voltage in a superimposed manner in a period other than the vertical transfer period and the horizontal transfer period.

7. The endoscope system according to claim 5, further comprising a superimposing circuit that (i) generates and outputs a vertical synchronization signal of one pattern during a vertical transfer period and a horizontal synchronization signal of one pulse during a horizontal transfer period, and (ii) generates and outputs a phase digital signal with a predetermined voltage in a superimposed manner in a period other than the vertical transfer period and the horizontal transfer period.

* * * * *